US008173578B1

(12) United States Patent
Walker et al.

(10) Patent No.: US 8,173,578 B1
(45) Date of Patent: May 8, 2012

(54) **BIOHERBICIDE AND METHOD FOR CONTROLLING GIANT *SALVINIA***

(75) Inventors: Harrell L. Walker, Ruston, LA (US); Lawrence R. Higginbotham, Ruston, LA (US); James A. Young, Simsboro, LA (US)

(73) Assignee: Louisiana Tech University Research Foundation, Ruston, LA (US)

( * ) Notice: Subject to any disclaimer, the term of this patent is extended or adjusted under 35 U.S.C. 154(b) by 210 days.

(21) Appl. No.: 12/642,107

(22) Filed: Dec. 18, 2009

(51) Int. Cl.
*A01N 63/04* (2006.01)
(52) U.S. Cl. .................................................. 504/117
(58) Field of Classification Search .................. None
See application file for complete search history.

(56) References Cited

U.S. PATENT DOCUMENTS 5,747,029 A * 5/1998 Walker et al. ............... 424/93.5
6,274,534 B1 * 8/2001 Boyette et al. ............... 504/117

OTHER PUBLICATIONS

Bonnet, A. L. M. 1955. Contribution à l'études des hydropteridees: recherches sur *Salvinia auriculata* Aublet. Annales des Sciences Naturelles, Botanique et Biologie Vegetale, Ills., 16:529-600.
Center, T. D., P. W. Tipping, J. A. Goolsby, and J. H. Everitt. 2001. Attack on Giant *Salvinia*. USDA-ARS Publication: http://www.nps.ars.usda.gov.
Flores, D. and J. W. Carlson. 2006. Biological control of giant *Salvinia* in east Texas waterways and the impact on dissolved oxygen levels. J. Aquatic Plant Management 44:115-121.
Forno, I. W. 1983. Native distribution of the *Salvinia auriculata* complex and keys to species identification. Aquatic Bot. 17:71-83.
Glomski, L. A. M., and K. D. Getsinger. 2006. Carfentrazone-ethyl for control of giant *Salvinia*. J. Aquatic Plant Management 44:136-138.
Holm, L. G., D. L. Plucknett, J. V. Pancho, J. P. Herberger. 1977. The World's Worst Weeds. University Press of Hawaii, Honolulu.
Loyal, D. S. and R. I. Crewal. 1966. Cytological study on sterility in *Salvinia auriculata* Aublet with a bearing on its reproductive mechanism. Cytologica 31:330-338.
Mitchell, D. S. 1973. *Salvinia molesta* sp. nov. Br. Fern Gaz. 10:251-252.
Mitchell, D. S. and N. M. Tur. 1975. The rate of growth of *Salvinia molesta* (*S. auriculata* Aubl.) in laboratory and natural conditions. Journal of Applied Ecology 12:213-225.
Owens, C. S., R. M. Smart, D. R. Honnell, and G. O. Dick. 2005. Effects of pH on growth of *Salvinia molesta* Mitchell. J. Aquatic Plant Management 43:34-38.
Owens, C. S., R. M. Smart, and R. M. Stewart. 2004. Low temperature limits of giant *Salvinia*. J. Aquatic Plant Management 42:91-94.
Owens, C. S., R. M. Smart, and G. O. Dick. 2004. Regeneration of giant *Salvinia* from apical and axillary buds following desiccation or physical damage. J. Aquatic Plant Management 42:117-119.

Room, P. M. and P. A. Thomas. 1986. Population growth of the floating weed *Salvinia molesta*: Field observations and a global model based on temperature and nitrogen. Journal of Applied Ecology 23:1013-1028.
Room, P. M., K. L. S. Harley, I. W. Forney, and D. P. Sands. 1981. Successful biological control of the floating weed *Salvinia*. Nature 294:78-80.
Thomas, P. A. and P. M. Room.1986.Taxonomy and control of *Salvinia molesta*. Nature 320:581-584.
Tipping, P. W. and T. D. Center. 2005. Population dynamics of *Cyrotobagous salviniae* on common *salvinia* in south Florida. J. Aquatic Plant Management 43:47-46.
Van Oosterhout, E. 2006. Salvinia control manual: Management and control options for *Salvinia* (*Salvinia molesta*) in Australia. NSW Department of Primary Industries (ISBN 0 7347 1747 4).
Whiteman, J. B. and P. M. Room. 1991. Temperatures lethal to *Salvinia molesta* Mitchell. Aquatic Bot. 40:27-35.
Louisiana Chemical Weed Management Guide. 2009. Louisiana State University Agricultural Center Publication No. 1655, 192 pp.
State and Federal Noxious Weeds List. USDA Plants Database. List of Invasive and Noxious Weeds. Plants Database. Natural Resources Conservation Service.
Weed Science Society of America: Lists of Common/Scientific Names.
H. Lynn Walker and Anthony M. Tilly. 1997. Evaluation of an Isolate of *Myrothecium verrucaria* from Sicklepod (*Senna obtusifolia*) as a Potential Mycoherbicide Agent. Department of Biological Sciences, Louisiana Tech University. pp. 104-112.
C. Douglas Boyette, Mark A. Weaver, Robert E. Hoagland, Kenneth C. Stetina. 2008. Submerged culture of a mycelial formulation, of a bioherbicidal strain of *Myrothecium verrucaria* with mitigated mycotoxin production. 24:2721-2726.
M.A. Weaver, R.E. Hoagland, C.D. Boyette, R.M. Zablotowicz, Macrocyclic Toichothecene Production and Sporulation by a Biological Control Strain of *Myrothecium verrucaria* is Regulated by Cultural Conditions, World Mycotoxin Journal, Feb. 2009; 2(1): 35-43.
P. Sheerama Kumar, S. Ramani and S.P. Singh, Natural Suppression of the Aquatic Weed, *Salvinia molesta* D.S. Mitchell, by two previously unreported fungal pathogens, J. Aquat. Plant Manage, 2005, 43: 105-107.
J. Douglas Oliver, A Review of the Biology of Giant *Salvinia* (*Salvinia molesta* Mitchell), J. Aquat. Plant Manage. 1993, 31: 227-231.

(Continued)

*Primary Examiner* — Alton Pryor
(74) *Attorney, Agent, or Firm* — Jones, Walker, Waechter, Poitevent, Carrere & Denegre, LLP

(57) ABSTRACT

A bioherbicide and method of use utilizing the fungus *Myrothecium verrucaria* for controlling *Salvinia molesta*. In typical applications, the fungus is applied with an adjuvant to *Salvinia molesta* in amounts effective to kill or suppress the *Salvinia molesta*. A strain of *Myrothecium verrucaria* is on deposit with the Department of Biological Sciences, Louisiana Tech University in Ruston, La., and with the patent collection of the International Mycological Institute in Surrey, United Kingdom, where it has been assigned deposit number IMI 368023.

8 Claims, No Drawings

OTHER PUBLICATIONS

D.K. Pandey, Inhibition of *Salvinia* (*Salvinia molesta* Mitchell) by *Parthenium* (*Parthenium hysterophorus* L.). I. Effect of Leaf Residue and Allelochemicals, Journal of Chemical Ecology., 1994, vol. 20, No. 12.

Pascal Leterme, Angela M. Londono, Jaime E. Munoz, Jeimmy Suarez, Carlos A. Bedoya, Wolfgang B. Souffrant, Andre Buldgen, Nutritional value of aquatic ferns (*Azolla filiculoides* Lam. and *Salvinia molesta* Mitchell) in pigs, Science Direct Annual Feed Science and Technology, 149 (2009) 135-148.

A. S. Mehta, A.P. Verma and B. Saran, Studies on Mineral Nutrition of *Salvinia molesta*. IV. Effect of Calcium Deficiency on Growth, Morphology and Anatomy, Geobios 14: 44-46-1987.

P.M. Room and M.H. Julien, Population-biomass dynamics and the absence of -3/2 self-thinning in the clonal weed *Salvinia molesta*, Australian Journal of Ecology (1994) 19, 26-34.

M. Iqbal Choudhary, Nadra Nahced, Ahmed Abbaskhan, Syed Ghulam Musharraf, Hina Siddiqui, Atta-ur-Rahman, Phenolic and other constituents of fresh water fern *Salvinia molesta*, M.I. Choudhary, et al, Phytochemistry 69 (2008) 1018-1023.

Lower Colorado River Giant Salvinia Task Force Action Plan, Draft (version Dec. 6, 2002).

Ryan M. Wersal and John D. Madsen, Invasive Species Fact Sheet, Giant *Salvinia* (*Salvinia molesta* D.S. Mitchell) Description, Distribution and Management, Aug. 2007.

J.H. Everitt, R.S. Fletcher, H.S. Elder, C. Yang, Mapping giant *Salvinia* with satellite imagery and image analysis, Environ Monit Assess (2008) 139: 35-40.

U.S. Army Engineer Research & Development Center, Linda S. Nelson, Chapter 13.4: Giant and Common Salvinia, 105-111.

Demonstration Project: Giant Salvinia, Toledo Bend Reservoir and Surrounding Areas in Louisiana and Eastern Texas, Environmental Assessment, Mar. 2001.

Georgina D. Arthur, Wendy A. Stirk, Ondrej Novak, Petr Hekera, Johannes van Staden, Occurrence of nutrients and plant hormones (cytokinins and IAA) in the water fern *Salvinia molesta* during growth and composing, G.D. Arthur, et al, Environmental and Experimental Botany 61 (2007) 137-144.

V. Usha Rani, S. Bhambie, A Study on the growth of *Salvinia molesta* Mitchell in relation to light and temperature, Aquatic Botany, 17 (1983) 119-124.

P.W. Tipping and T.D. Center, *Cyrtobagous salviniae* (Coleoptera: Curculionidae) Successfully Overwinters in Texas and Louisiana, Florida Entomologist 86(1), Mar. 2003, 92-93.

Linda S. Nelson, John G. Skogerboe, and Kurt D. Getsinger, Herbicide Evaluation Against Giant *Salvinia*, J. Aquat. Plant Manage. 2001, 39: 48-53.

D.G. McFarland, L.S. Nelson, M.J. Grodowitz, R.M. Smart and C.S. Owens, U.S. Army Corps of Engineers, *Salvinia molesta* D.S. Mitchell (Giant *Salvinia*) in the United States: A Review of Species Ecology and Approaches to Management, Aquatic Plant Control Research Program, Jun. 2004.

H. Lynn Walker, Evaluation of a Potential Bioherbicide for Control of Giant *Salvinia* (*Salvinia molesta* Mitchell), Jul. 7, 2009.

\* cited by examiner

BIOHERBICIDE AND METHOD FOR CONTROLLING GIANT *SALVINIA*

I. BACKGROUND

The invention described herein relates to a bioherbicide utilizing the fungus *Myrothecium verrucaria* for controlling *Salvinia molesta* Mitchell (SAMOS). *Salvinia molesta* is a floating tropical fern that is native to Brazil. *Salvinia molesta*—commonly known as giant salvinia—has been described as one of the two worst aquatic weeds in the world, along with water hyacinth. In the tropical and subtropical regions of the world where infestations occur, the impact of giant salvinia on human activities can be devastating. Because the plant is often introduced without its natural enemies, giant salvinia often becomes invasive, replaces native flora, and disrupts ecosystems. In addition to the United States, the plant has been reported in more than 20 countries.

A typical giant salvinia plant is comprised of units (ramets) of three leaves (fronds). Ramets are joined by underwater stems (rhizomes) that have apical and axillary buds. The two floating leaves are covered with numerous leaf hairs, which make these leaves resistant to wetting. Giant salvinia can be identified by the cage-like configuration of the leaf hairs. Each submerged leaf is finely dissected and these are often mistaken for roots. These modified leaves, and associated sporocarps, trail beneath the surface of the water and can be several feet in length.

Three growth stages have been identified: primary, secondary, and tertiary. Population densities and nutrient levels influence these growth patterns. At low populations densities, the plants remain in the primary stage of growth; however, as plants become more crowded, the growth pattern changes to secondary, and then to tertiary stages of growth. These growth patterns are well documented and have been described in detail elsewhere [See e.g., Van Oosterhout, E., *Salvinia control manual: Management and control options for salvinia* (*Salvinia molesta*) *in Australia*, NSW Department of Primary Industries (ISBN 0 7347 1747 4) (2006)]. Under ideal conditions, giant salvinia biomass can double in 3 days and reach levels of 400 tonnes of fresh weight per hectare (178.5 short tons per acre). These growth rates can exceed the capability of control by mechanical removal. Floating mats in the tertiary stage of growth can be multilayered—sometimes 2 feet thick—essentially blocking all sunlight penetration into the water.

*Myrothecium verrucaria*—a cosmopolitan, soil inhabiting fungus—has previously been shown to be effective in controlling various flowering seed plants. For instance, U.S. Pat. No. 5,747,029 (Walker et al.), hereby incorporated by reference, teaches methods for the biological control of various flowering seed plants (both monocot and dicot species) including sicklepod, pigweed, spurred anoda, jimsonweed, and hemp sesbania using Myrothecium verrucaria. U.S. Pat. No. 6,274,534 (Boyette et al.), also hereby incorporated by reference, describes the use of *Myrothecium verrucaria* for control of kudzu, also a dicot species.

While these works teach that *Myrothecium verrucaria* is effective in controlling a number of dicot species of flowering seed plants, they also document that there are a number of species of monocots and dicots that are resistant or immune to the bioherbicidal activity of the fungus. The bioherbicidal activity of the fungus could not be predetermined for specific species of flowering seed plants. In fact, effective control of a given species by *Myrothecium verrucaria* was shown to be more the exception than the rule.

The present invention describes the use of *Myrothecium verrucaria* to control giant salvinia, a species of aquatic fern. Apparently, *Myrothecium verrucaria* has not been reported as a pathogen of giant salvinia. Moreover, ferns are taxonomically very different from the flowering seed plants in that ferns do not produce flowers, fruits, or seeds. In the six kingdom classification system, the Kingdom Plantae places ferns in the phylum Polypodiophyta, while flowering seed plants are placed in the phylum Magnoliophyta, which is divided into the classes Magnoliopsida (dicots) and Liliopsida (monocots). Because of the taxonomic and biological differences that exist between the flowering seed plants and the ferns, the bioherbicidal activity Myrothecium verrucaria toward ferns, and in particularly giant salvinia, could not have been predicted based on the prior art.

II. SUMMARY

The present invention is directed to a means for the effective biological control of giant salvinia (*Salvinia molesta* Mitchell) using the fungus *Myrothecium verrucaria*. In an embodiment, the fungus is isolated, produced, compositioned, and applied to giant salvinia by methodology taught in U.S. Pat. No. 5,747,029 (Walker et al.) and U.S. Pat. No. 6,274,534 (Boyette et al.), both of which are herein incorporated by reference.

III. DEPOSIT OF BIOLOGICAL MATERIAL

*Myrothecium verrucaria* (Alb. and Schwein) Ditmar ex Fr. is on deposit in the patent collection of the International Mycological Institute (Bakeham Lane, Englefield Green, Egham, Surrey TW20 9TY, United Kingdom) under the terms of the Budapest Treaty, Jun. 21, 1995, and has been assigned accession number IMI 368023. It is also on deposit with the Department of Biological Sciences, Louisiana Tech University, Ruston, La. The address of the Department of Biological Sciences is: Louisiana Tech University, Harrell L. Walker, Department of Biological Sciences, P.O. Box 3179, TS., Ruston, La. 71272.

IV. DESCRIPTION

The *Myrothecium verrucaria* (IMI 368023) used in this invention was isolated from diseased plants of sicklepod. The fungus was cultured in a corn flour/soyflour/sucrose (CFSF) growth medium. The composition per liter of growth medium comprised 15 g corn flour; 15 g soyflour; 30 g sucrose; and 3 g calcium carbonate. One liter of the medium was dispensed into 2 liter Erlenmeyer flasks, plugged using cotton plugs, and sterilized by autoclaving at 121° C. for 25 minutes. In other embodiments, the corn flour can be replaced with corn meal (15 g/L), resulting in a corn meal/soyflour/sucrose (CMSF) growth medium. The fungus can also be cultured by a variety of other means known in the art, such as those disclosed in U.S. Pat. No. 5,747,029 (Walker). However, the CMSF growth medium has been reported to produce mycelia preparations of *Myrothecium verrucaria* that exhibit reduced levels of macrocyclic trichothecene toxins. [See Boyette, C. D., M. A. Weaver, R. E. Hoagland, and K. C. Stetina, *Submerged culture of a mycelial formulation of a bioherbicidal strain of Myrothecium verrucaria with mitigated mycotoxin production*, World J. Microbiol. Biotechnol. 24:2721-2726 (2008)].

Mycelial preparations were prepared from cultures that were grown on bench-top rotary shakers (approximately 150 rpm) under ambient laboratory conditions. The shake-flask cultures were harvested 4 to 10 days after inoculation. The fungal cultures, including residual growth medium, were homogenized in a laboratory blender for approximately one minute. An aqueous solution was then formulated by adding an adjuvant to the homogenate, and the mixture was homogenized for an additional one minute. As used herein, an adjuvant is broadly defined as any substance other than water which is not in itself a herbicide but which enhances or is intended to enhance the effectiveness of the herbicide with which it is used. Adjuvants are understood to encompass surfactants (wetting agents), stickers (sticking agents), plant penetrants, compatibility agents, buffers and acidifiers, drift retardants, defoaming agents, and thickeners. While not intended to limit the range of suitable adjuvants, examples of adjuvants that were used to enhance bioherbicidal activity of Myrothecium verrucaria were: Sil-MES™ 100 (Proprietary blend of organosilicone non-ionic surfactant, alcohol ethoxylate and methylated seed oil)(Drexel Chemical Company, Memphis, Tenn.); MES-100™ (Methylated seed oil blend and other principal functioning agents)(Drexel Chemical Company, Memphis, Tenn.); Surf-Ac® 820, (non-ionic surfactant comprising alcohol ethoxylate, alkylphenol ethoxylate, plus constituents ineffective as spray adjuvants)(Drexel Chemical Company, Memphis, Tenn.); Silwet L-77® (Polyalkyleneoxide modified heptamethyltrisiloxane, a registered product of GE Silicones) (Helena Chemical Company, Collierville, Tenn.); Aqua-King® Max (Nonylphenol polyethylene glycol ether, glycol and free fatty acids organic phosphatic acids, dimethypolysiloxane, plus constituents ineffective as spray adjuvants)(Estes, Inc. Irving, Tex.); and Thoroughbred® (Proprietary blend of polyalkyleneoxide modified polydimethylsiloxane and nonionic surfactants, plus constituents ineffective as spray adjuvants)(Estes, Inc., Irving, Tex.).

The experimental parameters used in the examples below are not intended to limit the scope of this invention. Modification of factors such as inoculum concentrations, parameters for inoculum production, adjuvants, application methods, and other factors, would be expected to influence efficacy of this invention. Parameters were selected to enable detection of interactions, to document the relationship of this invention to the prior art, and to illustrate that the unique and surprising characteristics of this invention were not obvious and could not have been predicted from the prior art.

EXAMPLE 1

The response of Salvinia molesta to an inoculation of Myrothecium verrucaria was tested in a replicated greenhouse study. Giant salvinia plants in the primary growth stage (mixed with duckweed [Lemna minor]) were placed in nine plastic containers (21.6 cm×34.3 cm) that were partially filled (11.8 L) with tap water. The giant salvinia was added to cover approximately one-half of the surface area of each container. Thus, there were nine experimental units.

Myrothecium verrucaria was grown in the CFSF growth medium for 6 days. The 6-day-old culture was homogenized using a laboratory blender. The mycelial homogenate was diluted (1:1) using distilled water. Sil-MES™ 100 was then added to obtain an aqueous composition of Myrothecium verrucaria having a Sil-MES™ 100 concentration of 0.625% (v/v).

The experimental units were divided into the following groups: untreated giant salvinia plants; giant salvinia plants sprayed with an aqueous composition comprising 0.625% (v/v) Sil-MES™ 100; and giant salvinia plants sprayed with an aqueous composition comprising homogenized mycelium of Myrothecium verrucaria plus 0.625% (v/v) Sil-MES™ 100. Aerosol sprayers were utilized for the spray applications, and the spray applications were made until the leaves were fully wetted. Each treatment and control was replicated three times. Following the applications, the plants were incubated on greenhouse benches and monitored for disease development.

Disease ratings for the giant salvinia were made using a 0 to 4 rating scale. Disease evaluations were made 2, 3, and 4 days after inoculation.

TABLE 1

Response of Salvinia molesta to Myrothecium verrucaria in Greenhouse Studies[a]
Disease Ratings[b]

| Time (days) | Untreated | Adjuvant Only[c] | M. verrucaria + Adjuvant[d] |
|---|---|---|---|
| 2 | 0 ± 0 | 0.5 ± 0 | 3.5 ± 0 |
| 3 | 0 ± 0 | 0.5 ± 0 | 3.5 ± 0 |
| 4 | 0 ± 0 | 0.4 ± 0.1 | 3.4 ± 0.1 |

[a]Mean values from three replications, ± standard error of mean
[b]Disease rating scale:
0 = no injury
1 = 25% of leaf area exhibited necrosis
2 = 50% of leaf area exhibited necrosis
3 = 75% of leaf area exhibited necrosis
4 = 100% of leaf area exhibited necrosis, no green buds apparent
[c]Sil-MES ™ 100 (0.625%)
[d]M. verrucaria + Sil-MES ™ 100 (0.625%)

As shown in Table 1, the giant salvinia plants exhibited significant necrosis when treated with an aqueous composition comprising Myrothecium verrucaria plus 0.625% adjuvant. Greater than 75% of the leaf area exhibited necrosis when treated with the fungus-adjuvant aqueous composition. In contrast, the adjuvant-only aqueous composition was shown to be ineffective in controlling the giant salvinia, with less than 25% of the leaf area exhibiting necrosis.

EXAMPLE 2

The response of Salvinia molesta to an inoculation of Myrothecium verrucaria was tested in a replicated field study. Myrothecium verrucaria was evaluated using a giant salvinia infestation growing at the Lake Bistineau State Park, Webster Parish, La.

Myrothecium verrucaria was grown in the CFSF growth medium for 10 days. The 10-day-old culture was homogenized using a laboratory blender. The mycelial homogenate was diluted (1:1) using distilled water. Sil-MES™ 100 was then added to obtain an aqueous composition having a concentration of Myrothecium verrucaria plus 6% (v/v) adjuvant.

Nine experimental units of giant salvinia plants were enclosed in 1 m² quadrants using floating frames constructed with 3.81 cm PVC pipe. The experimental units were divided into the following groups: untreated giant salvinia plants; giant salvinia plants sprayed with an aqueous composition comprising 6% (v/v) Sil-MES™ 100; and giant salvinia plants sprayed with an aqueous composition comprising homogenized mycelium of Myrothecium verrucaria plus 6% (v/v) Sil-MES™ 100. A compressed $CO_2$ sprayer (R & D Sprayers, Opelousas, La.) was utilized for the spray applications, and the spray applications were made until the leaves were fully wetted. Each treatment and control was replicated three times.

Following the applications, the plants were monitored for disease development. Disease ratings for the giant salvinia plants were made using a 0 to 4 rating scale. Disease evaluations were made over a two-week period after inoculation.

TABLE 2

Response of *Salvinia molesta* to
*Myrothecium verrucaria* in Lake Studies[a]
Disease Ratings[b]

| Time (days) | Untreated | Adjuvant Only[c] | *M. verrucaria* + Adjuvant[d] |
|---|---|---|---|
| 1 | 0 ± 0 | 3.8 ± 0 | 3.8 ± 0 |
| 2 | 0 ± 0 | 3.5 ± 0 | 3.9 ± 0 |
| 3 | 0 ± 0 | 3.0 ± 0 | 3.7 ± 0.1 |
| 4 | 0 ± 0 | 2.8 ± 0 | 3.4 ± 0.1 |
| 9 | 0 ± 0 | 2.0 ± 0 | 3.9 ± 0 |
| 11 | 0 ± 0 | 2.0 ± 0 | 3.9 ± 0 |
| 14 | 0 ± 0 | 2.0 ± 0 | 3.9 ± 0 |

[a]Mean values from three replications, each experimental unit enclosed one square meter; ± standard error of mean
[b]Disease rating scale:
0 = no injury
1 = 25% of leaf area exhibited necrosis
2 = 50% of leaf area exhibited necrosis
3 = 75% of leaf area exhibited necrosis
4 = 100% of leaf area exhibited necrosis, no green buds apparent
[c]Sil-MES ™ 100 (6%)
[d]*M. verrucaria* + Sil-MES ™ 100 (6%)

As shown in Table 2, the giant salvinia exhibited significant necrosis when treated with an aqueous composition comprising *Myrothecium verrucaria* plus 6% (v/v) adjuvant. Almost 100% of the leaf area of the giant salvinia exhibited necrosis when treated with the fungus-adjuvant aqueous composition. The efficacy of the fungus-adjuvant aqueous composition was observed within 24 hours of initial inoculation. A slight decrease in effectiveness was noted on days 3 and 4, although approximately 85% of the leaf area still exhibited necrosis. The fungus-adjuvant aqueous composition's efficacy returned to near 100% by day 9 and remained stable through day 14.

The adjuvant-only aqueous composition was shown to be less effective in controlling the giant salvinia. Initially, the giant salvinia exhibited necrosis when treated with the adjuvant. However, the efficacy of the adjuvant-only aqueous composition steadily decreased over the observation period.

The aforementioned results indicate that the mortality of giant salvinia is correlative to the presence of the fungus Myrothecium verrucaria. Giant salvinia was effectively controlled with the application of a herbicidally effective amount of the fungus Myrothecium verrucaria. Given the demonstrated activity of the exemplified strain of the fungus of the invention, one of ordinary skill in the art will recognize that all of the strains of the fungus likely can be used for controlling giant salvinia. Thus, the present invention contemplates all of the strains of Myrothecium verrucaria. Further, given the taxonomic and biological similarities, the present invention contemplates

*Myrothecium verrucaria* being effective for the biological control of other Salvinia species, such as Salvinia minima (common salvinia), *Salvinia auriculata* (eared salvinia), *Salvinia biloba* (lobed salvinia), and *Salvinia herzogii* (Herzog salvinia).

The experimental parameters used in examples cited for this invention were selected to enable detection of interactions, to document the relationship of this invention to the prior art, and to illustrate that the unique and surprising characteristics of this invention were not obvious and could not have been predicted from the prior art. The experimental parameters are not intended to limit the scope of this invention. For instance, while a composition comprising *Myrothecium verrucaria* plus 6% (v/v) adjuvant was utilized in field tests, one skilled in the art will readily appreciate that herbicidally effective inoculum concentrations may vary widely from the concentrations utilized herein. In other embodiments, the novel bioherbicide of the present invention can be formulated as a suspension, an emulsion, or an invert emulsion in either aqueous or non-aqueous (i.e., solid) media. The carriers for aqueous and solid formulations containing the fungus of the invention can be either inert or active; i.e., they can either affect or not affect the virulence of the fungus of the invention. Potential active carriers include, but are not limited to, surfactants (wetting agents), stickers (sticking agents), plant penetrants, compatibility agents, buffers and acidifiers, drift retardants, defoaming agents, and thickeners. Potential inert carriers include water, talc, silica, vermiculite, corn cob grits, kaolin clay, and calcium alginate formulations. These bioherbicidal compositions can be applied to the plant as foliar sprays, dusts, granules, or any other means known in the art.

While the preferred embodiments have been described above, it will be recognized and understood that various modifications may be made in the invention and the appended claims are intended to cover all such modifications which may fall within the spirit and scope of the invention. Modification of factors such as inoculum concentrations, parameters for inoculum production, adjuvants, application methods, and other factors, would be expected to influence efficacy of this invention.

What is claimed is:

1. A method for the control of *Salvinia molesta* comprising the application of a herbicidally effective amount of *Myrothecium verrucaria* to said *Salvinia molesta*.

2. The method of claim 1, wherein said *Myrothecium verrucaria* is applied in the form of an aqueous composition.

3. The method of claim 2, wherein said aqueous composition further comprises an active carrier.

4. The method of claim 3, wherein said active carrier is an adjuvant.

5. The method of claim 2, wherein said aqueous composition is applied to said *Salvinia molesta* as a foliar spray.

6. The method of claim 1, wherein said *Myrothecium verrucaria* has the identifying characteristics of strain IMI 368023.

7. A method for the biological control of *Salvinia molesta* comprising the application of *Myrothecium verrucaria* and an adjuvant to said *Salvinia molesta*.

8. The method of claim 7, wherein said *Myrothecium verrucaria* has the identifying characteristics of strain IMI 368023.

* * * * *